(12) United States Patent
DesMarteau et al.

(10) Patent No.: US 6,794,492 B2
(45) Date of Patent: Sep. 21, 2004

(54) PERFLUOROALKYL COMPOUNDS AND THEIR METHODS OF USE AND MANUFACTURE

(75) Inventors: Darryl DesMarteau, Clemson, SC (US); Vittorio Montanari, Milan (IT)

(73) Assignee: Clemson University, Clemson, SC (US)

( * ) Notice: Subject to any disclaimer, the term of this patent is extended or adjusted under 35 U.S.C. 154(b) by 286 days.

(21) Appl. No.: 09/817,507

(22) Filed: Mar. 26, 2001

(65) Prior Publication Data

US 2001/0046960 A1 Nov. 29, 2001

Related U.S. Application Data

(60) Provisional application No. 60/195,342, filed on Apr. 5, 2000.

(51) Int. Cl.⁷ .............................. C07K 5/08; C07K 7/00
(52) U.S. Cl. ............................. 530/331; 514/2; 514/16; 514/17; 514/18; 514/19; 530/330; 530/345; 562/553; 562/445; 570/123
(58) Field of Search ................................. 514/16–19, 2; 530/330, 331, 345; 562/553, 445; 570/123

(56) References Cited

U.S. PATENT DOCUMENTS 6,001,824 A * 12/1999 Nakanishi et al. .......... 514/151
6,168,913 B1   1/2001 Hochlowski et al. .......... 435/4
6,288,187 B1   9/2001 Armand ...................... 526/240

OTHER PUBLICATIONS

Umemoto, T., Journal of Fluorine Chemistry 31(1), 37–56, 1986.*
Umemoto, T., Bull. Chem. Soc. Jpn. 60, 3307–13, 1987.*
DesMarteau, D., Chemical Communications (Cambridge) (20), 2241_2242, 1998.*
Carr, S. (Biomedical Mass Spectrometry 8(2), 51–61, 1981).*
McDowell (Biochem 35, 3328, 1996).*
Hoeltzli (Biochem 33, 5502, 1994).*
Duewel (Biochem 36, 3404, 1997).*

* cited by examiner

*Primary Examiner*—Christopher S. F. Low
*Assistant Examiner*—David Lukton
(74) *Attorney, Agent, or Firm*—Dority & Manning, P.A.

(57) ABSTRACT

Fluorinated alkyl compounds may be used as reaction intermediates or reaction products in polymerizing amino acid structures into peptides. Fluorinated methyl groups have been found to be particularly useful. A compound having a fluorinated methyl group such as that set forth below:

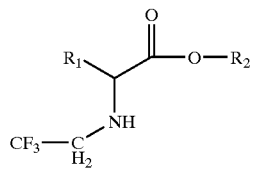

wherein R is selected from the group consisting of: alkyls, hydrogen, aryls, aromatic compounds, amines, sulfur-containing alkyl groups, sulfur-containing aryl groups, and heterocyclic compounds may be utilized alone, or reacted in combination with other amino acids, to form a dipeptide, or polypeptide.

25 Claims, 12 Drawing Sheets

Figure 1: Direct preparation of an N-alpha-trifluoroethyl amino acid from the commercially available tert-butyl ester Figure 2: Examples of products prepared from an N·alpha-trifluoroethyl amino acid under standard coupling conditions

PERFLUOROALKYL COMPOUNDS AND THEIR METHODS OF USE AND MANUFACTURE

REFERENCE TO PREVIOUS APPLICATION

This application claims priority from previously filed Provisional Application No. 60/195,342 filed on Apr. 5, 2000.

BACKGROUND OF THE INVENTION

Perfluoroalkyl iodide compounds have been known for some time. It has been observed that iodonium salts having a fluoroalkyl and an aryl group are strong alkylation agents with useful reaction chemistry.

Recently, it has been reported that fluorine-containing amino acids have been actively investigated in view of their high potential for biological studies and medical applications. See "The First Fluoroalkylation of Amino Acids and Peptides in Water Utilizing the Novel Iodonium Salt $(CF_3SO_2)_2NI(Ph)CH_2CF_3$", DesMarteau and Montanari. Synthetic routes to fluorinated amino acids normally involve several steps using fluorinated building blocks, mostly obtained by the conversion of carbon heteroatoms to C—F bonds. A more direct approach involves fluoroalkylations. Cysteine and related amino acids and peptides can be alkylated by alkyl halides or esters if both the substrate and alkylating reagant can be solubilized in mixed water organic solvents or in liquid ammonia. The novel iodonium salts disclosed in the above referenced publication are generally stable to water.

Other investigators have reported that hypervalent iodine compounds are useful reagants or reactive intermediates. See Umemoto and Gotoh, "Synthesis, Properties, and Reactivity of (1H, 1H-Perfluoroalkyl)- and (1H-Perfluoro-1-alkenyl)aryliodonium Triflates and Their Analogs". The hypervalent iodines may carry fluoro-alkyl or alkenyl groups, and they have shown useful properties in part because of the high electronegativity of the fluoro groups. However, many of these reaction schemes are sensitive to the presence of water, and therefore could not be expected to be useful in biological applications or other aqueous applications of peptide chemistry.

Unfortunately, most reaction schemes to prepare di-peptides or long peptide chains using amino acids have the added difficulty that an unprotected —COOH group of the amino acid will react readily with the adjacent nitrogen of the N-alkyl amino acid. Thus, in many cases it is impossible to provide for coupling of one amino acid with another amino acid because an unprotected —COOH is reactive. Typically, it has been required in the past to convert the —COOH group to an ester group having an alkyl R attached so that the amino acid molecule will not condense with itself, as shown below:

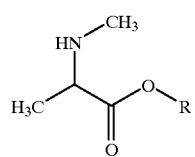

A chemistry reaction scheme that facilitates the reaction or combination of amino acids with each other to form dipeptides or polypeptides, in a way that does not require the —COOH group to be first converted to an ester as shown above, would be very useful. A reaction sequence or compound that is capable of deactivating the nitrogen group (i.e. the —NH) in an amino acid, such as that set forth below, would be highly desirable.

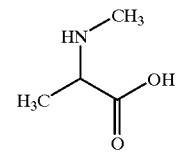

Preferably, such a group or composition would reduce the reactivity of the —NH group in the molecule above such that it does not react as quickly, thereby facilitating the formation of di-peptides, polypeptides, and so forth. The —NH needs to be deactivated so that the —COOH group does not condense with the —NH group within one amino acid, but instead reacts in a desirable manner to form compounds having more than one amino acid in sequence.

SUMMARY OF THE INVENTION

Surprisingly, it has been discovered that certain fluorinated compounds may be successfully used as reaction agents in accomplishing the polymerization of useful amino acids structures into peptides. Novel lipophilic building blocks that can be used with amino acids have been discovered. Fluorinated methyl groups have been found to be particularly useful.

Compounds and reaction schemes have been discovered that may provide a lipophilic moiety which is more readily absorbed across the blood brain barrier, making them particularly useful for biological applications as applied to pharmaceutically active compounds of many types. For example, many proteins involved in osteoporosis, arthritis, and cancer may be reacted with compounds containing fluoro groups (i.e. —$CF_3$; —$CH_2$—$CF_3$, and the like) to produce altered structures that are more lipophilic than their fully H-saturated counterparts, providing more biological mobility, more stability, and increased biological activity.

Certain compounds have been found to be useful as biological building blocks to generate many types of pharmaceutically useful and active compounds. These building blocks avoid the unintentional or undesirable condensation of an amine group with an adjacent —COOH group, thereby allowing for combination of amino acid and similar compounds to be coupled together in a way that promotes biological activity.

In one application of the invention, a compound having the generic formula below is provided:

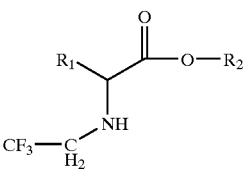

in which the $R_1$ and $R_2$ group is selected from the group consisting of: alkyls, hydrogen, aryls, aromatic compounds, amines, sulfur-containing alkyl groups, sulfur-containing aryl groups, and heterocyclic compounds; and $R_2$. In many applications, the R group will be chosen so as to provide a compound having an amino acid base structure. Further, the compound above may be reacted to form a dipeptide, a tripeptide, or a multi-peptide structure having biological activity. These structures may be incorporated into animal or human proteins having biological application.

In another aspect of the invention, the di-peptide having the chemical formula:

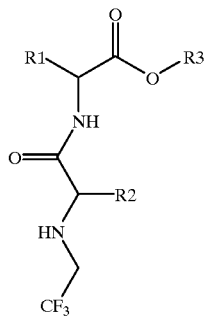

is shown, in which $R_1$, $R_2$, and $R_3$ each are selected from the group consisting of: alkyls, hydrogen, aryls, aromatic compounds, amines, sulfur-containing alkyl groups, sulfur-containing aryl groups, and heterocyclic compounds.

In yet another aspect of the invention, a peptide or peptide chain having the generic structure set forth below is disclosed:

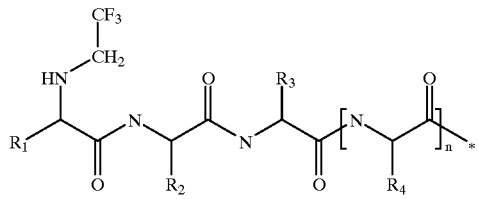

In the above embodiment of the invention, the $R_1$, $R_2$, $R_3$ and $R_4$ groups are independently selected from the group consisting of: alkyls, hydrogen, aryls, aromatic compounds, amines, sulfur-containing alkyl groups, sulfur-containing aryl groups, and heterocyclic compounds. A repeating sequence denoted by a long chain peptide having multiple -n groups is provided, and -n may have a value of as little as 1 to as much as several hundred thousand.

In other aspects of the invention, the novel compounds having fluorinated carbon atoms could be used in forensic applications for tagging or providing a chemical signature on compounds for later detection by mass spectrometry, or other analytical techniques. For example, it would be possible to prepare novel fluorine and iodine containing analogs of compounds known to bind brain receptors. Fluorine could be introduced as a 2,2,2-trifluoroethyl group. A methoxy or methylenedioxy functionality on an aromatic ring could provide for rapid iodination. Using this method, it would be possible to "tag" or chemically identify compounds so that if and when they are later used to manufacture drugs or illegal substances, analytical chemical techniques could be used to confirm the source of the starting materials. This could assist providing linking evidence in narcotics enforcement.

In biological and medical applications, this "tagging" procedure could be used to follow the course of compounds as they traverse the blood brain barrier, and determine by radioiodine imaging and similar techniques the location of substances that have been introduced into a human or animal. Thus, medical investigators and researchers could use the compounds of this invention to choose an appropriate fluorinated material among a wide variety made by the alkylation methods disclosed herein.

In some applications, it would be possible and desirable to take biological material from an individual, fluorinate carbon atoms in a preselected manner, and then re-introduce the material, facilitating a measure of the accumulation of such materials in the body and various locations within the body.

Further, other compounds containing a —$CF_3$ group have been found to have anti-cancer activity. In particular, dipeptides of tyrosine/isoleucine with a —$CF_3$ group attached to a nitrogen (—NH) group are found to have anti-cancer activity, as one example. Other compounds and amino acid moieties, dipeptides, tripeptides, and polypeptides likewise are likely to have anticancer activity.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The invention is described by a general and direct synthesis of fluoroalkyl-substituted molecules from common amino acids. In the discussion that follows, numbers are provided in parenthesis (i.e. "(1)", "(2)" and the like) to denote or number the compounds shown and listed in this text for easier reference). Further, FIGS. 1 and 2 show a reaction sequence described below, and referenced such as 2a, 3a, 4a, 5a and the like refer to FIGS. 1–2.

A rapid, high-yielding alkylation provides for aqueous media at ambient temperature, consisting in the transfer of a 2,2,2-trifluoroethyl group from the iodonium salt $(CF_3SO_2)_2NI(Ph)CH_2CF_3$         (1)

to amino acid side chains. Because large amounts of compound 1 above may be prepared readily, compound 1 may be used as a discovery tool for bioactive substances.

Figure 1:
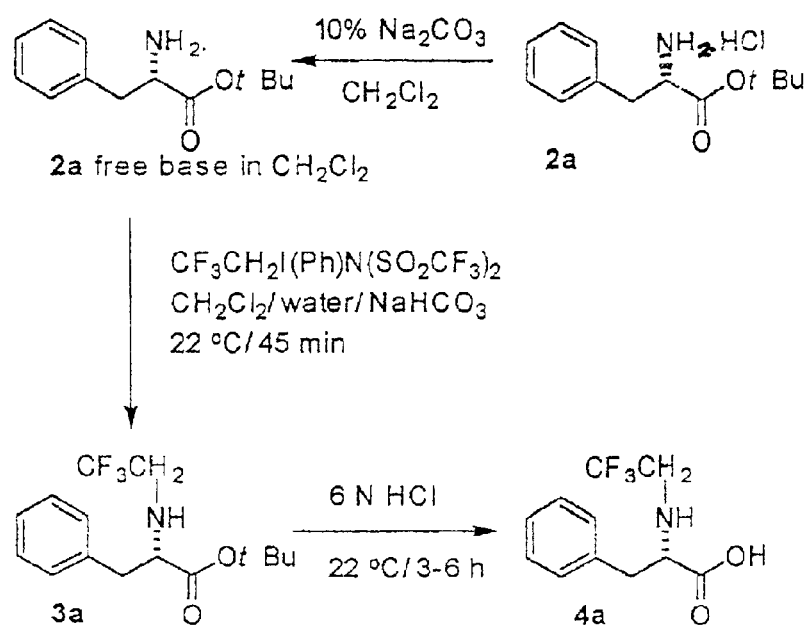
FIG. 1 shows a direct preparation of an N-alpha-trifluoroethyl amino acid from the commercially available tert-butyl ester, as one example of the invention.
Figure 2:
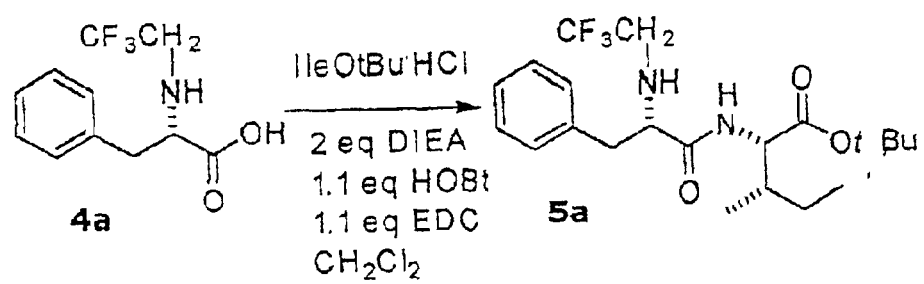
FIG. 2 shows products prepared from an N-alpha-trifluoroethyl amino acid under standard coupling conditions.

It has been found that amino acid esters are alkylated by compound 1 at the alpha-nitrogen under convenient two-phase conditions ($CH_2Cl_2$/water/$NaHCO_3$)(see FIG. 1). Standard peptide synthesis has been found to apply to the free acids (4a–c). Thus, any number of fluorinated structures incorporating compounds 4a—(see Table 1 below) may be synthesized for systematic evaluation.

The preparation of 4a–c by a procedure shown in FIG. 1 and representative examples of standard couplings giving amide compounds 5a–b and dipeptides 6a–c (see FIG. 2, Table 1). Racemization of compound 4 under coupling was not apparent by 300 and 500 MHz NMR. Table 1 is shown below:

TABLE 1

Coupling Reactions of 4a, 4b and 4c

| Trifluoroethyl amino acid | Second component | Product | Yield % |
|---|---|---|---|
| 4a | (+)1-amino-2-indanol | 5$^a$ | 68$^b$ |
| 4a | (−)1-amino-2-indanol | 5$^b$ | 80$^b$ |
| 4a | (L)IleOBu$^t$ | 6$^a$ | 64 |
| 4a | (L)AlaOMe | 6$^b$ | 64–95$^{c,d}$ |
| 4a | (D)AlaOMe | 6$^c$ | 62 |
| 4a | (D,L)AlaOMe | 6$^d$ | 24$^{be}$ |
| 4a | (L)ValOMe | 6$^e$ | 73–90$^c$ |
| 4a | (D,L)ValOMe | 6$^f$ | 88 |
| 4b | (L)AlaOBu$^t$ | 6$^g$ | 74 |
| 4b | (L)Glu(OAll)OAll | 6$^h$ | 97 |
| 4c | (L)PheOBu$^t$ | 6$^i$ | 95 |

The lettered footnotes provided above reference the following:
$^a$All reactions on a 0.50 mmol scale, with 1.1 eq HOBt, 1.1 equivalents EDAC, 2 eq DIEA unless indicated.
$^b$after chromatography; not necessary for the other products.
$^c$55% using DCC in place of EDAC.
$^d$4 sets of conditions.
$^e$with water/$NaHCO_3$ in place of DIEA.

Commercially available amino acid t-butyl ester compounds 2a–c were employed as starting materials. In fact, t-butyl esters are not only especially stable to bases, but also are readily hydrolyzed by dilute acids. This combination of properties has made possible the direct procedure shown in FIG. 1. The procedure requires partitioning between organic and aqueous phase, and the amino acid product compounds 4a–c are obtained in a pure state. Chromatographic isolation of the intermediate ester compounds 3a–c is possible but generally unnecessary.

The reaction shown in FIG. 2 whereby compounds 4a–c produce compounds 5a–b and 6a–h is ubiquitous for peptide synthesis in solution. Very high yields and very low or no racemization that is observed. However, one would customarily expect the usual alkyl- and aryloxycarbonyl-protecting groups. $CF_3CH_2$ is, however, an alkyl group. Nevertheless, even using this fluorinated alkyl group, it was surprisingly found that the behavior of compound 3a and that of Z-phenylalanine are essentially the same under the standard coupling procedure of FIG. 2.

In further exploring these compounds, the issue of peptide chemistry and possible racemization of the amino acid that undergoes the coupling was addressed. The system used was one comprising a water-soluble carbodimide EDAC, the additive hydroxy benzotriazole (HOBt) and disopropyl ethyl amine (DIEA), to provide high yields and little or no racemization.

The products were analyzed using 200 or 300 MHz $^1$H and 188 MHz $^{19}$F NMR only, the latest experiments (Table 1, entries) are supported by 500 MHz $^1$H and 470 MHz $^{19}$F.

One result included the preparation of the two diastereomeric amide compounds 5a and 5b from (+) and (−) 2-amino indanol, which were single compounds by NMR. Similarly, (L) isoleucine t-butyl ester with its two stereocenters produced a single diastereomer compound (6a) using 3a. The dipeptide compounds 6b and 6c could be compared with 6d as a reference and were single compounds by the same NMR analysis. When the higher field NMR became available, the eight combinations (four preparations each of 6b and 6e) of 3a with (L)AlaOMe and (L)ValOMe were used as the incoming aminoacids, $CH_2Cl_2$ or DMF as the solvent, and 1 or 2 molar equivalents of DIEA were examined. In this specification, the standard abbreviations for the amino acids used by persons of skill in the art shall be used throughout. The methyl esters of (L)Ala and (L)Val were used in this review because the corresponding (D) and (D,L) forms are commercially available. Thus, it was possible to use compounds 6d and 6f as NMR standards. The signals corresponding to diastereomers were not detected in any run.

The best-yielding conditions according to this screening experiment were used for more reactions, where the trifluoroethyl amino acid is tyrosine (4b) or valine (4c) and the second amino acid has the more practical t-butyl or allyl ester O-protection. The dipeptides and are also essentially pure as obtained from workup.

The reactivity of the novel aminoacids represented by compounds 4a–c is reversed relative to the other known alkyl aminoacids, due primarily to the presence of the fluorinated carbon atom. Reaction occurs only at the carboxyl function, under the routine conditions used for N-protected aminoacids in peptide synthesis.

In general, commonly known "protecting" groups standard in the industry, such as Boc, Z, and formyl, occur in synthetic bioactive molecules and are evaluated as structural units in pharmaceutical design. While structure-activity relationship is a very complex subject, a simple chemical function of such "protection" is that metabolic deactivation by oxidative dealkylation is retarded or prevented. That is precisely the known utility of a fluoroalkyl residue.

Thus compound 1 has proven to be a discovery tool that has a wide variety of applications, and preparative amounts of the amino acids represented by compounds 4a–c may be produced. Most importantly, they undergo standard peptide chemistry, even while fluorinated, which provides an opportunity for study of amino acids in vivo. This unexpected property of compound 4 provides for a large number of potentially bioactive fluoroalkylated substances. Finally, it is also desirable to continue to study the direct transformation of preassembled peptides as an alternative. For example, compound 1 and (L)Glu(L)PheOMe (aspartame, 8) provide in one step $CF_3CH_2$(L)Glu(OCH$_2$CF$_3$)(L)PheOMe 9 (80% yield, analytically pure).

Heteroatom-alkyl functions are often a part of the structure of bioactive substances. The in vivo process of oxidative dealkylation of such functions is a challenge to the development of medicinal drugs. It can render a candidate drug ineffective by preventing it from reaching its targets, or may produce toxic metabolites or requiring too high dosages.

General methods to form the heteroatom-fluoroalkyl linkage, that could be used for drug discovery purposes, have been the subject of investigation. As a general purpose fluoroalkylation reagent with several desirable properties, the iodonium salt $CF_3SO_2OI(Ph)CH_2CF_3$ was introduced by Umemoto and Gotoh in 1986 (see previous article referenced above). It could transfer a trifluoroethyl group to various nucleophiles in methylene chloride as the solvent, under very mild conditions and in good yields, and it was quite simply prepared on a 100 g scale. The reactions of reagent described in the article by Umemeto is promoted by non-nucleophilic organic bases such as collidine or 2,6-di-t-butyl pyridine.

Preparation of N-alpha-Trifluoroethyl Aminoacids

The fluoroalkylation at the alpha nitrogen of amino acids, to give the heretofore unreported N-alpha-trifluoroethyl aminoacids, gave inconsistent results when first attempted on amino acid methyl esters. At the time, this seemed attributable to the lower nucleophilicity of an amino acid compared to an alkyl amine. First, the reactivity order is SH >>COO—>>$NH_2$>>OH, that is, a carboxylate anion will be selectively alkylated by compound 1 in preference to an amino group.

Secondly, a water-soluble primary amine will undergo alkylation twice to give high yields of an N-alkyl-N,N'-bis-(1,1,1)-trifluoroethyl amine. The tertiary amine is normally the major product from a water-soluble primary amine even if only one equivalent of compound 1 is used. Bis-trifluoroethyl lysine is a typical example. After the first trifluoroethyl group has been attached, the resulting amine of general formula $RNHCH_2CF_3$ cannot be more nucleophilic than the alpha-amino function of an amino acid. Thus the reaction of compound 1 with amino acid esters was reexamined as a challenging reaction that should be given one more chance. Considering that compound 1 alkylates a carboxylate function, and that a methyl ester is more subject to hydrolysis than higher alkyl esters, then it follows that if hydrolysis occurs, a trifluoroethyl ester will be formed rapidly. This ester is eventually also hydrolyzed under the reaction conditions, so that compound 1 is consumed to trifluoroethanol but little of the desired product is formed.

Commercially available amino acid t-butyl esters are especially stable to bases, and readily hydrolyzed by dilute acids. This combination of properties has made them very popular in peptide synthesis.

A Discovery Tool to Prepare Fluoroalkyl Compounds

A 1,1,1-trifluoroethyl group, unlike regular alkyl groups, could have the advantage of not suffering dealkylative oxidation in vivo. This was proven by the first N-1,1,1-trifluoroethyl compounds to enter medical practice, the tranquilizer Halazepam® and the closely similar Quazepam®, developed at Schering (both are believed to be trademarks of Shering Plough Corporation). The peculiarity of 1,1,1-trifluoroethyl compounds is shown in the Schering synthesis. The first step is the reaction between anilines and 1,1,1-trifluoroethyl tosylate which yields trifluoroethyl anilines by refluxing in dichloromethane. In the next step, trifluoroethyl anilines form amides with bromoacetyl bromide by reflux in benzene, apparently with loss of HBr gas. No corresponding reactions of alkylamines are known. Ammonia reacts with trifluoroethyl halides only under special conditions. Significantly, the reaction of a hydroquinone, not a good nucleophile, with trifluoroethyl trifluoromethanesulfonate is used to prepare a life-saving drug, the antiarrhytmic Flecainide® (3M Company; registered trademark of the 3M Company).

Drug discovery now relies on the combinatorial synthesis of very many potentially active structures in the shortest time. This restricts chemical methods to the fastest and most reliable; in particular, peptide bond formation. If an active substance is discovered, its preparation in larger amounts is addressed separately.

The novel compound (reagant) 1, which is water-stable, easily made and storable for very long time periods, gives access to a large variety of fluoroalkyl structures. Otherwise, the known preparative methods require "designing the molecule around fluorine". This is too time consuming in the discovery stage of drug research. By utilizing a discovery tool like compound 1, the large-scale preparative aspects may be considered when the necessity arises. In that case, simple and bulk-produced building blocks such as trifluoroethylamine and trifluoroacetaldehyde acetals are readily available.

We have prepared and investigated a novel class of unnatural aminoacids, the N-alpha-trifluoroethyl aminoacids. Their reactivity is reversed relative to the known N-alkyl aminoacids. Reaction occurs only at the carboxyl function, under the routine conditions used for N-protected aminoacids in peptide synthesis. The effective "protection" of the NH function results from both the electron withdrawing effect and the size of the 1,1,1-trifluoroethyl group. We must remark now that "protecting" groups such as Boc, Z, and formyl occur in synthetic bioactive molecules and are evaluated as structural units in pharmaceutics design. While structure-activity relationship is a very complex subject, a simple chemical function of such "protection" is that metabolic deactivation by oxidative dealkylation is retarded or prevented. That is precisely one of the known utilities of a fluoroalkyl residue. Unexpectedly, the novel N-alpha-trifluoroethyl amino acids behave entirely as the familiar N protected amino acids (Z, Boc, Fmoc, etc.). The structures of these groups are known by persons of skill in the art. Further, the trifluoroethyl group is not meant to be a removable protecting group: simply, any number of novel peptides containing N-alpha-trifluoroethyl amino acid units become available by the standard operating procedure of carbodimide-promoted condensation. The chemistry of compound 1 gives the opportunity to approach the discovery of novel fluoroalkyl compounds per se rather than as analogs of known materials. Thus compound 1 proves to be a useful discovery tool.

EXAMPLE 1

Following the reported preparation on a larger scale, $HN(SO_2CF_3)_2$ (18.00 g, 64 mmol), $CF_3CH_2I(OCOCF_3)_2$ 26.50 g (61 mmol) and benzene (6.2 mL, 70 mmol) were reacted in CFC 113 (50 mL) yielding compound 1 as a powder (30.7 g after freeze-drying (54 mmol, 89%). Crystallization ($CH_2Cl_2$, 4 mL/g, −20° C.) gave 27.3 g (79% overall) of compound 1 as transparent prisms, mp 77–79° C., dec. 105–120° C. (TGA, 5° C./min).

EXAMPLE 2

A typical procedure for compound 4 was as follows: Phenylalanine t-butyl ester hydrochloride (2a of FIG. 1) (2.540 g, 9.85 mmol) was suspended in 75 mL $CH_2Cl_2$. Water (75 mL) and $Na_2CO_3$ (7 g) were added and the mixture stirred 30 min. The clear organic layer was separated. $NaHCO_3$ (1.00 g, 11.9 mmol), water (70 mL) and compound 1 (6.02 g, 10.62 mmol) were added with stirring at 20° C. After 45 min the $CH_2Cl_2$ phase was separated and washed with 3×100 mL water. It was then stirred twice at 20° C. with 150 mL 6N HCl for 3 h. The combined aqueous HCl solutions were evaporated to dryness yielding 2.30 g (77%) of crystalline compound 2a hydrochloride monohydrate, mp 159–160° C.

EXAMPLE 3

Another procedure was performed as follows: $CF_3CH_2$(L)PheOH.HCl.$H_2O$ (compound 4a)(150 mg, 0.50 mmol), (L)AlaOMe.HCl (70 mg, 0.50 mmol), HOBt.H$_2$O (75 mg, 0.55 mmol) and EDAC (106 mg, 0.55 mmol) were suspended in CH$_2$Cl$_2$ (5.0 mL). The suspension was cooled in ice/water, and DIEA (175 alpha-L, 1.0 mmol) was added rapidly by syringe. The reaction was run in the stoppered flask for 1 h in ice, then for 3 h at 22° C. The reaction mixture was diluted to 50 mL with CH$_2$Cl$_2$, and washed with 0.1 N NaHCO$_3$ (50 mL), 50 mL 0.5 N HCl, and 2×50 mL water. After drying on Na$_2$SO$_4$, evaporating, and pumping at 0.05 mmHg, compound 5a (158 mg, 95%) was obtained as a white powder with a melting point of about 73–76° C.

EXAMPLE 4

Certain compounds of the type described herein exhibit anti-cancer activity. FIGS. 3–9 show several compounds which are believed to have such activity, although these Figures and their chemical representations are by no means exhaustive of all the compounds of this type which may have anti-cancer activity in humans or animals.

The testing below was conducted by the United States Public Health Service, Department of Health and Human Services. The National Cancer Institute (NCI) in vitro antitumor screening test consists of about 60 human tumor cell lines against which compounds are tested at a minimum of 5 concentrations at 10 fold dilutions. A 48 hour continuous drug exposure protocol is used, and a sulforhodamine B (SRB) protein assay is used to estimate cell viability or growth.

Figure 3:
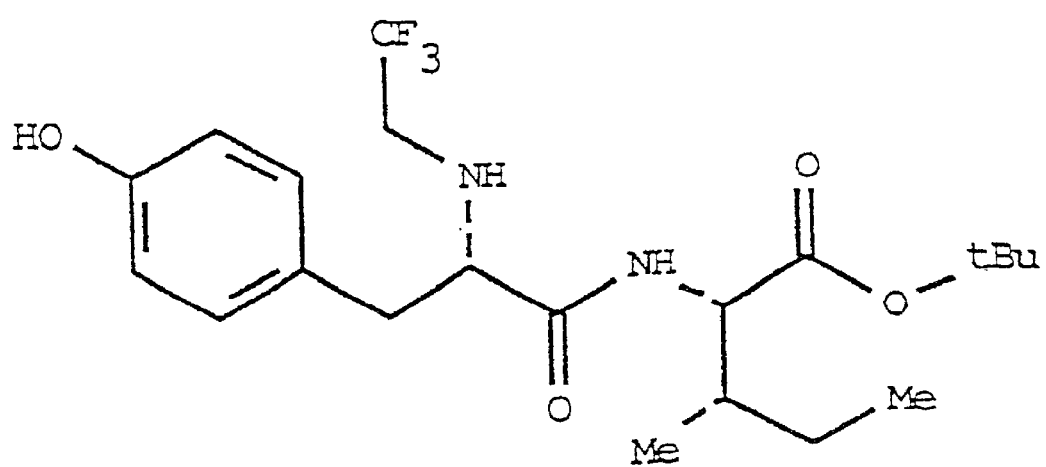
FIGS. 3–9 depict chemical structures of various compounds which are believed to show anti-cancer activity in human or animal tissue cell lines.
Figure 4:
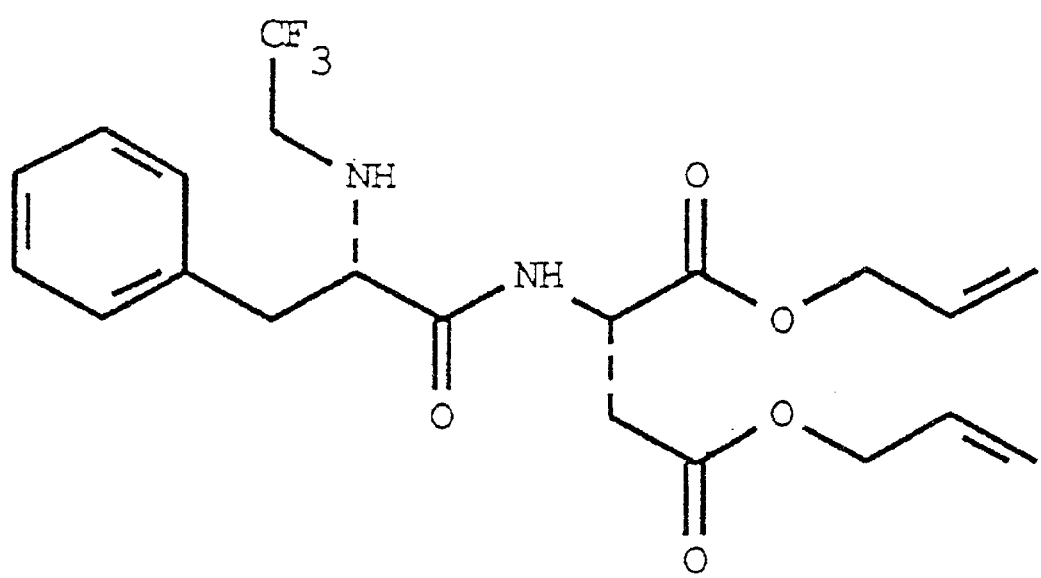
Figure 5:
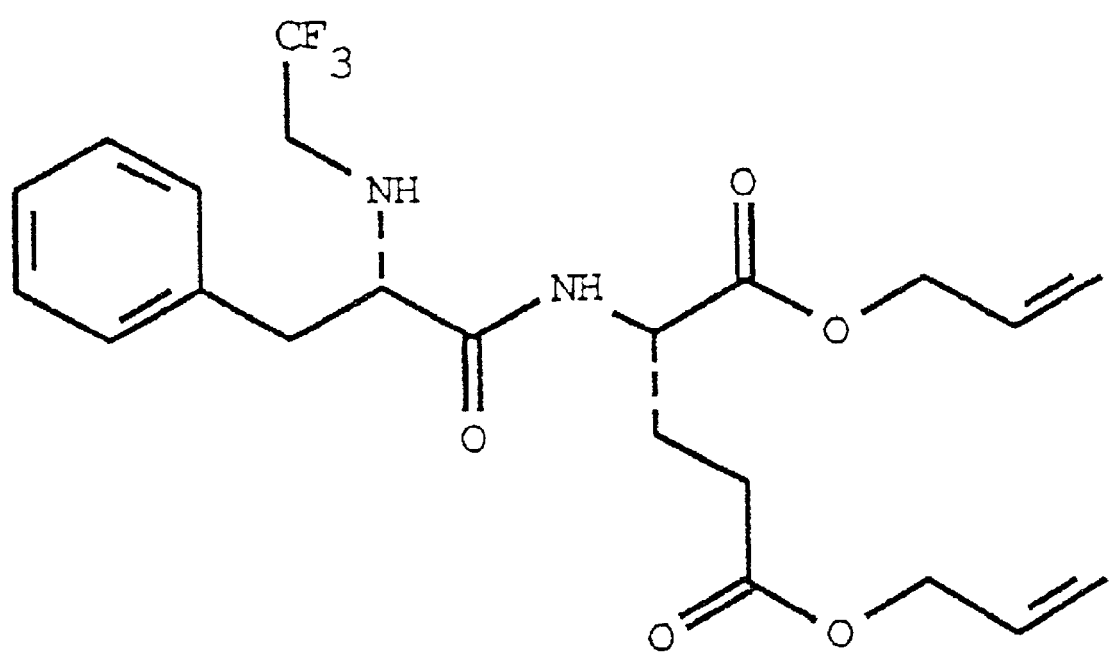
Figure 6:
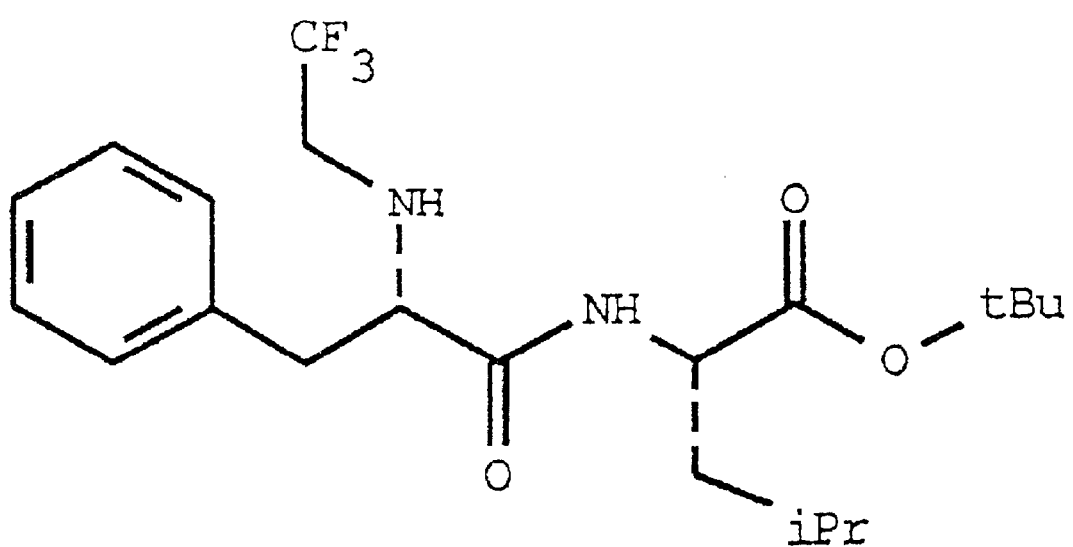
Figure 7:
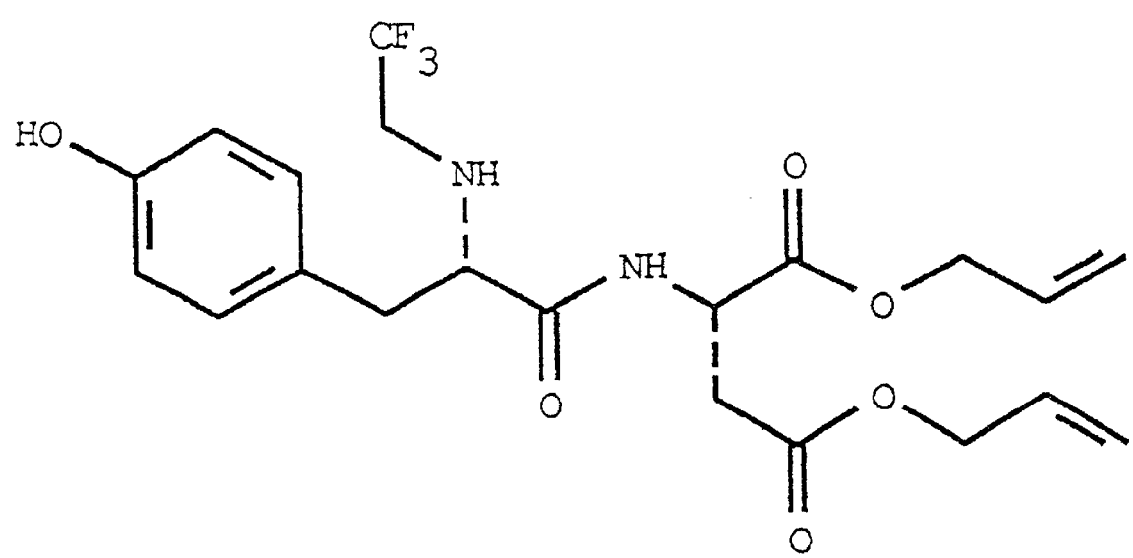
Figure 8:
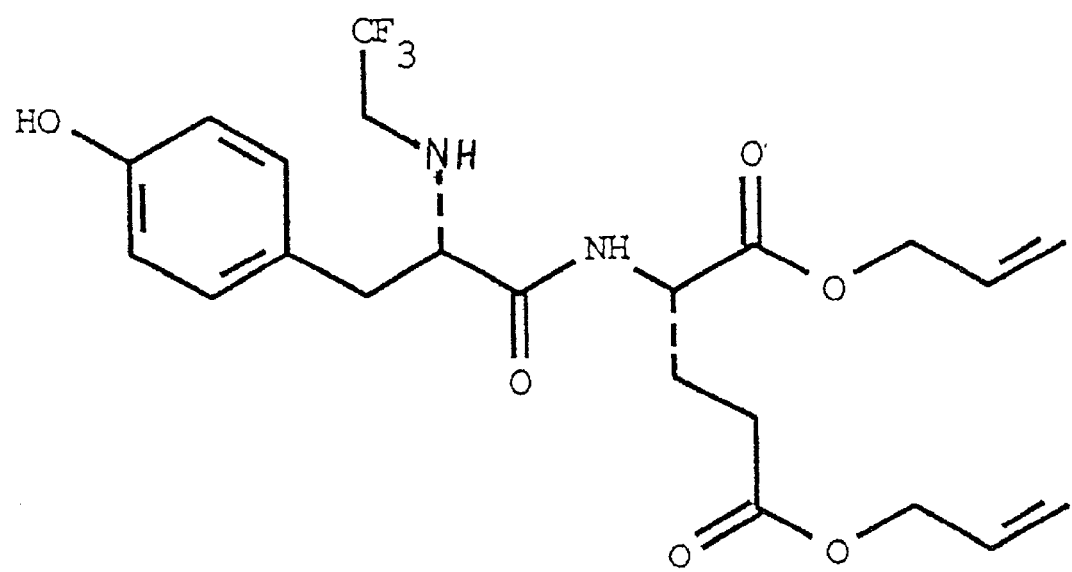
Figure 9:
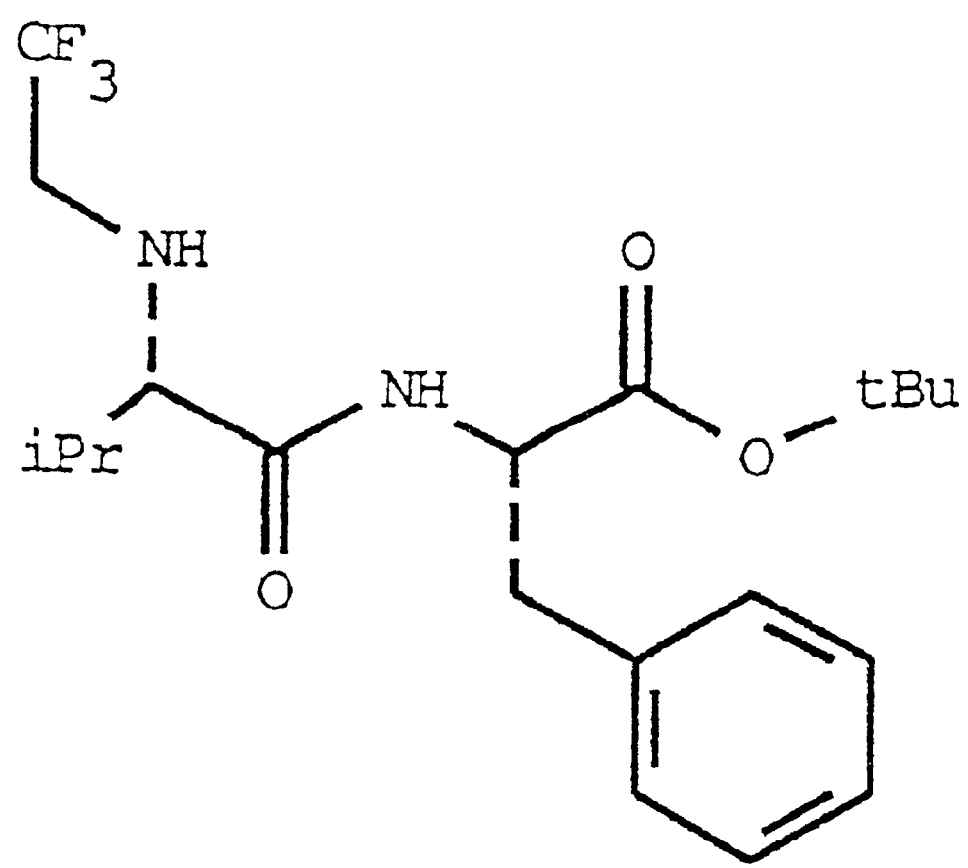
Figure 13:
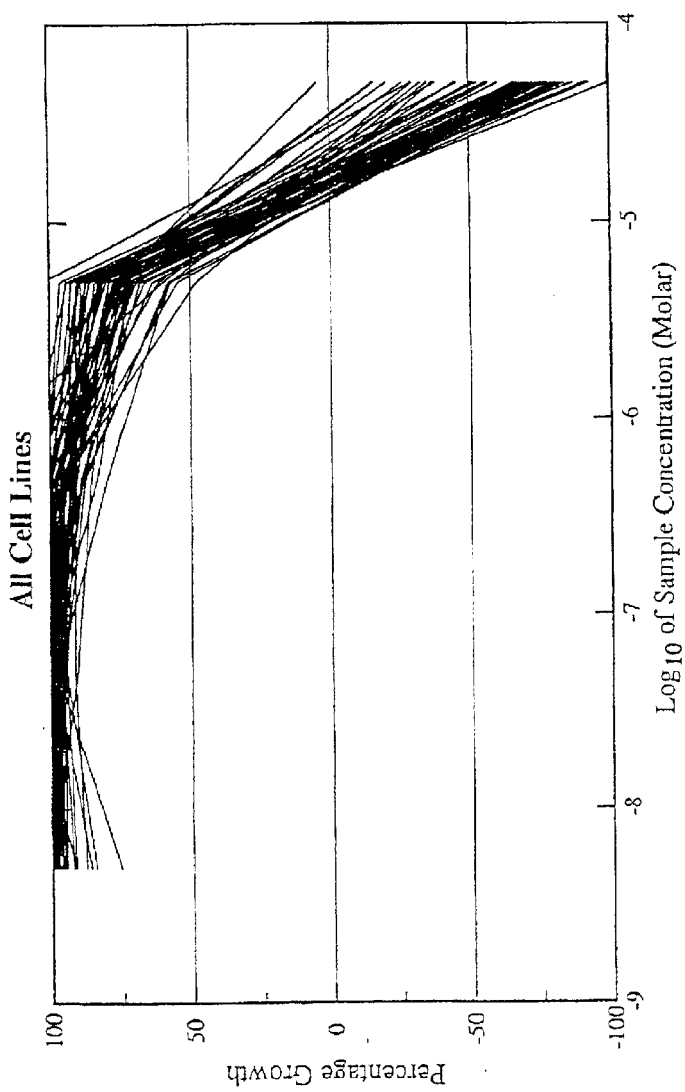
FIG. 13 shows a dose response curve for the compound shown in FIG. 3 herein.

Data for the compound shown in the attached FIG. 3 which was tested according to the National Cancer Institutes Developmental Theraputics Program (dose response curves) is shown in attached FIG. 13. That is, the data shown in FIG. 13 corresponds to testing of the compounds shown in FIG. 3 herein. For example, the compound shown in FIG. 3 was evaluated in a three-cell line, and was found to have growth percentages as follows:

| Prefix (NSC) | Sample Concentration | Growth Percentages | | | |
|---|---|---|---|---|---|
| | | lung | breast | CNS | activity |
| S712619 | 5.00 E-05 Molar | −77 | −57 | −75 | active |

EXAMPLE 5

Fluorine and iodine containing analogs of compounds are known to bind brain receptors. Fluorine may be introduced as the 2,2,2-trifluoroethyl group. The methoxy or methylenedioxy functionality on the aromatic ring makes fast iodination possible. A potential application of this invention is in the field of brain imaging. Because iodine is uncommon and fluorine is essentially absent in biological chemistry, it is possible to use these compounds as tracers.

Figure 10:
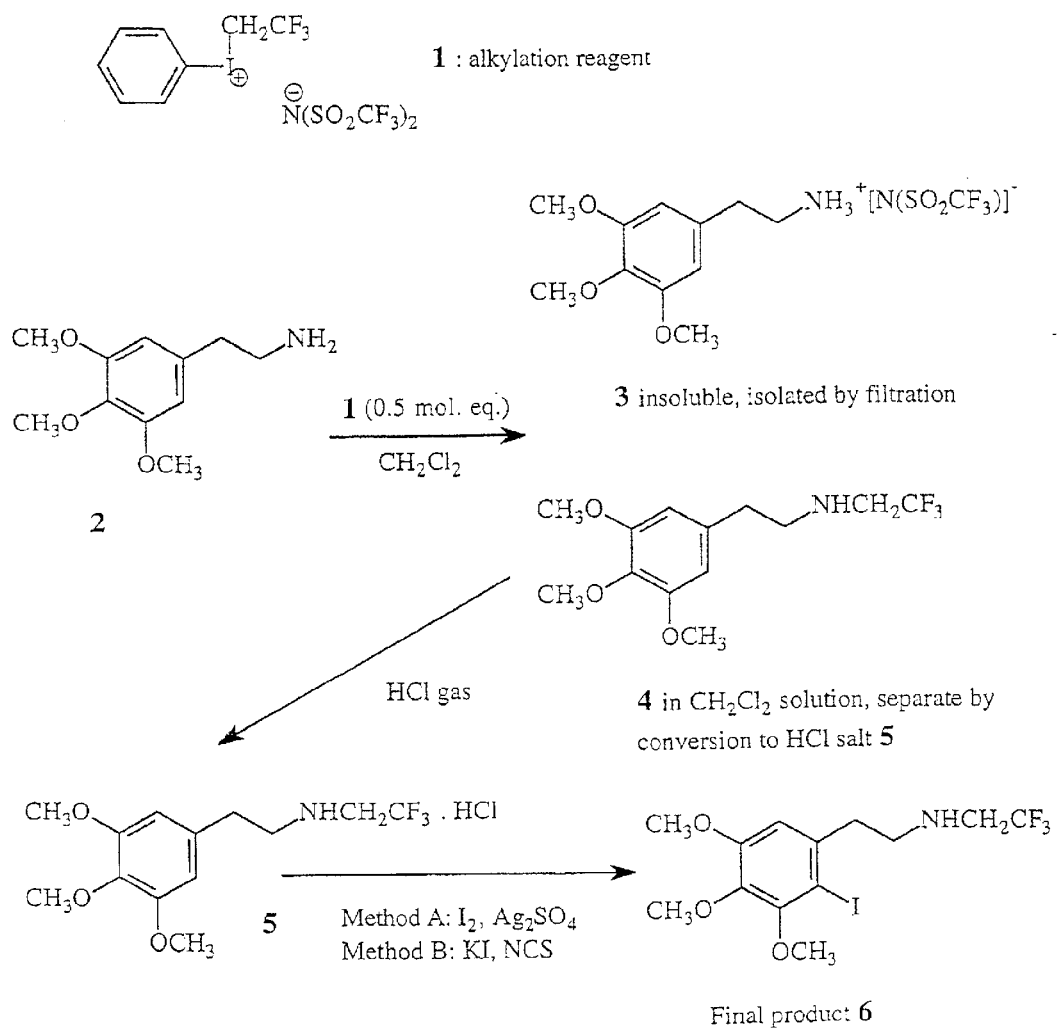
FIGS. 10–12 are directed to reaction sequences showing use of the compounds of this invention as chemical tracers.
Figure 11:
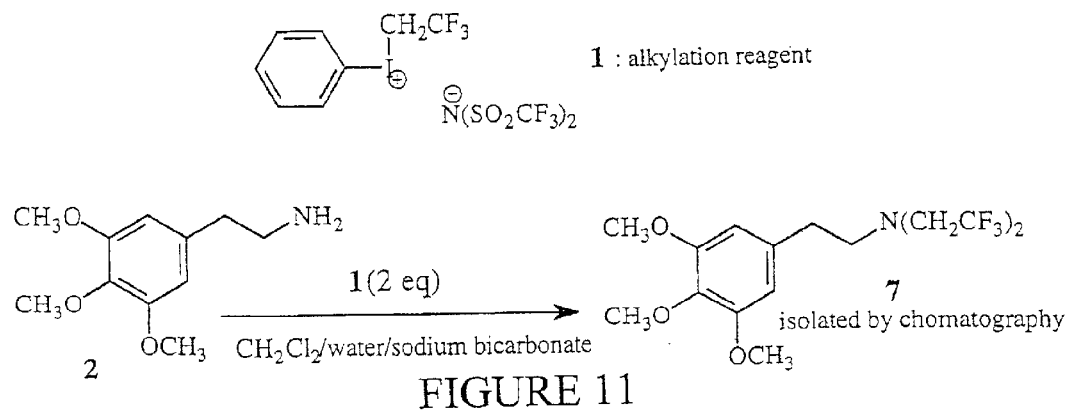
Figure 12:
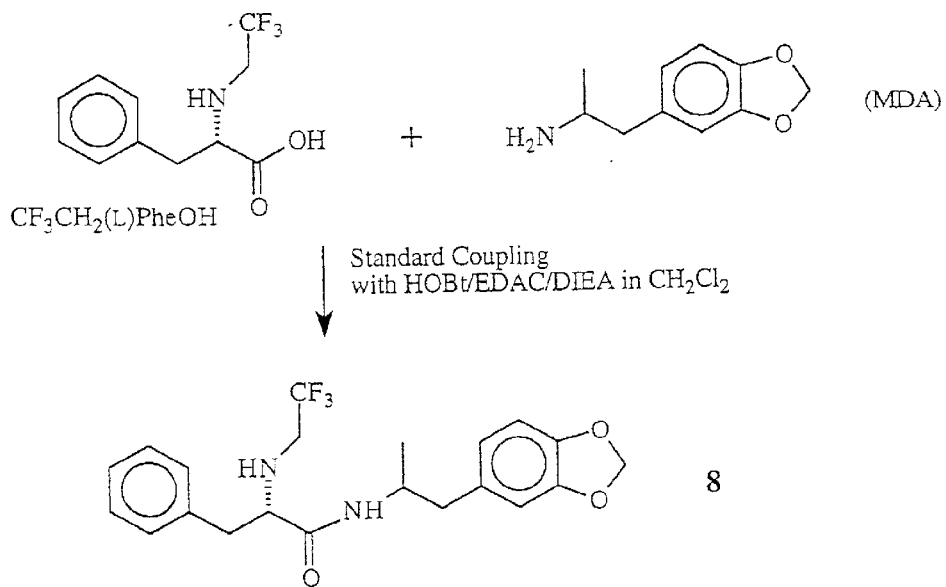

Safrol may be used to prepare by literature methods 3,4 methylenedioxy amphetomine (i.e.: "MDA" herein) in sufficient amounts to carry out reactions represented with mescaline in FIGS. 10 and 11. About 100 mg of MDA per reaction are necessary. The amount of Safrol used will depend upon the actual yields of MDA obtained and whether use of the separate enantiomers of MDA in the reaction sequence are employed. Related substances such as MDE and MDMA can be prepared from Safrol, but they are not expected to undergo any different chemistry relative to FIGS. 10–11. Mescaline can be converted to N-2,2,2-trifluoroethyl mescaline, N—N'(bis)-2,2,2-trifluoroethyl mescaline and into mescaline-(N,N'-bis trifluoromethylsulfonyl)amide salt as shown in FIG. 10. The total amount used typically is 500 mg or less.

EXAMPLE 6

A technique for introducing 2,2,2-trifluoroethyl (or higher fluoroalkyl) residue into molecules having potential bioactivity is shown below. First, such a residue is known to impart useful properties, especially resistance to oxidative dealkylation in vivo. In medicinal chemistry, preparation of Quazepam®, Flecainide®, and the like may be used in evaluating a drug discovery approach. Alkylation of amines may be carried out very simply with minimal or no need for purification steps. Two 2,2,2-trifluoroethyl groups are readily introduced on nitrogen when the starting primary amine has some solubility in water. Both the monoalkyl product (compound 4 or its salt 5 in FIG. 10) and the dialkyl product (compound 7 in FIG. 11) can be prepared relatively quickly from any starting amine and evaluated for activity.

Imaging may determine the concentration and distribution of the compounds in tissues. Iodine may be introduced into fluorinated substances by the same chemical routes reported for radioiodine imaging. Medical investigators will choose the best fluorinated material, among the wide variety which are made available by this method, utilizing iodine isotopes.

EXAMPLE 7

It is possible to prepare novel amides by exploiting the surprising property of N(alpha)trifluoroethyl aminoacids to undergo condensation at the carboxyl function, while the alpha-nitrogen is relatively inert (giving "inverse activity"). The unprecedented amino acid molecule may retard or prevent enzymatic hydrolysis.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

What is claimed is:

1. An N-alpha trifluoroethyl amino acid compound having the generic formula:

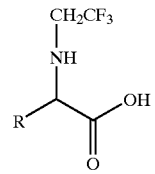

wherein R is selected from the group consisting of alkyls, hydrogen, aromatic groups, amines, thioalkyl groups, sulfur containing aromatic groups, heterocyclic groups, and combinations thereof.

2. N-alpha trifluoroethyl amino acid compound of claim 1, in which R comprises an aromatic ring.

3. The N-alpha trifluoroethyl amino acid compound of claim 1, in which the N-alpha trifluoroethyl amino acid is N-alpha trifluoroethyl phenylalanine.

4. The N-alpha trifluoroethyl amino acid compound of claim 1, in which the N-alpha trifluoroethyl amino acid is N-alpha trifluoroethyl tyrosine.

5. The N-alpha trifluoroethyl amino acid compound of claim 1, in which the N-alpha trifluoroethyl amino acid is N-alpha trifluoroethyl valine.

6. An N-alpha trifluoroethyl amino acid ester compound having the generic formula:

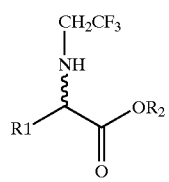

wherein R1 and R2 are independently selected from the group consisting of alkyls, hydrogen, aromatic groups, amines, thioalkyl groups, sulfur containing aromatic groups, heterocyclic groups, and combinations thereof.

7. The N-alpha trifluoroethyl amino acid ester compound of claim 6, which R1 comprises an aromatic ring.

8. The N-alpha trifluoroethyl amino acid ester compound of claim 6, in which R2 comprises an alkane.

9. The N-alpha trifluoroethyl amino acid ester compound of claim 7, in which the alkane comprises a carbon chain having less than about 6 carbons.

10. The N-alpha trifluoroethyl amino acid ester compound of claim 7, in which R2 comprises a t-butyl group.

11. A peptide comprising a terminal N-alpha trifluoroethyl amino acid.

12. The peptide of claim 11, wherein the peptide comprises the general structure:

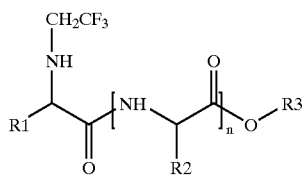

wherein R1, R2, and R3 are independently selected from the group consisting of alkyls, hydrogen, aromatic groups, amines, thioalkyl groups, sulfur containing aromatic groups, heterocyclic groups, and combinations thereof; and n is greater than or equal to 1.

13. The peptide of claim 12, wherein the peptide is a dipeptide.

14. The peptide of claim 12, wherein the dipeptide has the general formula:

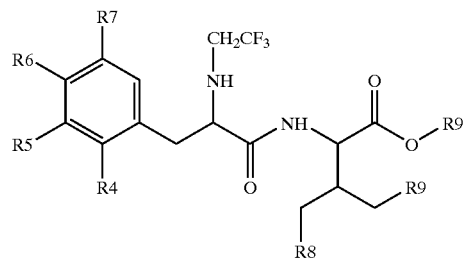

wherein R4, R5, R6, R7, R8, and R9 each are independently selected from the group consisting of alkyls, hydrogen, aromatic groups, amines, thioalkyl groups, sulfur containing aromatic groups, heterocyclic compounds, and combinations thereof.

15. The peptide of claim 13, wherein R1 comprises a phenyl group.

16. The peptide of claim 15, wherein the peptide has the structure represented by:

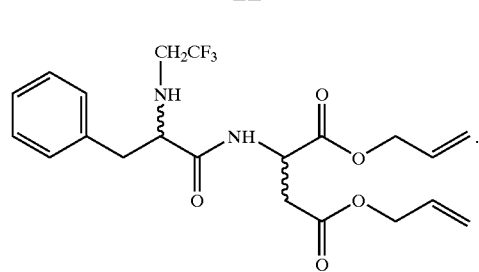

17. The peptide of claim 15, wherein the peptide has the structure represented by:

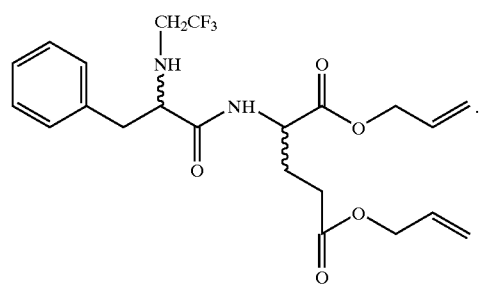

18. The peptide of claim 17, wherein the peptide has the structure represented by:

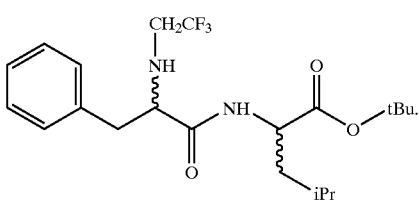

19. The peptide of claim 15, wherein R1 comprises a p-methylphenol group.

20. The peptide of claim 19, wherein the peptide has the structure represented by:

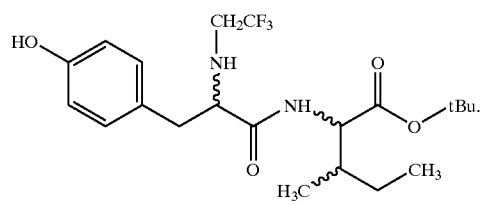

21. The peptide of claim 19, wherein the peptide has the structure represented by:

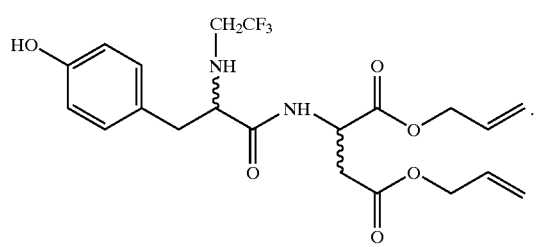

22. The peptide of claim 19, wherein the peptide has the structure represented by:

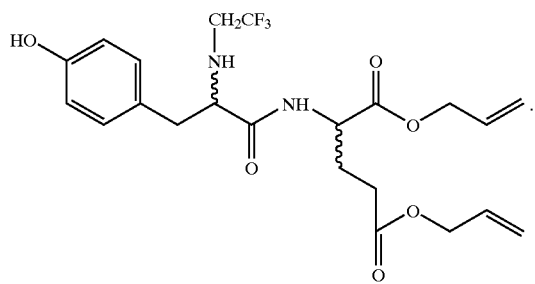
23. The peptide of claim 13, wherein the peptide has the structure represented by:
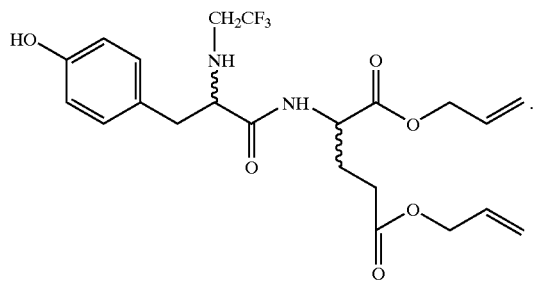
24. The peptide of claim 11, wherein the peptide comprises the structure of:
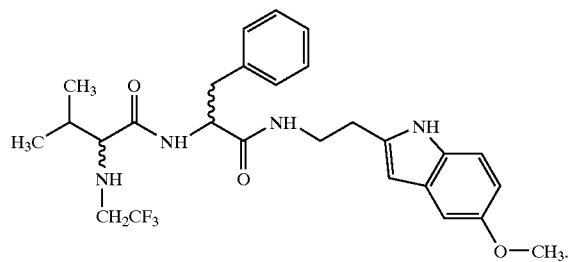
25. The peptide of claim 11, wherein the peptide comprises the structure of:
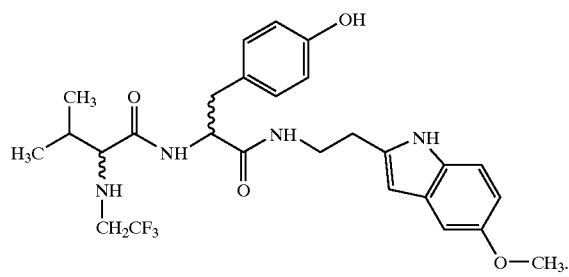
* * * * *

UNITED STATES PATENT AND TRADEMARK OFFICE
CERTIFICATE OF CORRECTION

PATENT NO.   : 6,794,492 B2
DATED        : September 21, 2004
INVENTOR(S)  : Darryl DesMarteau and Vittorio Montanari It is certified that error appears in the above-identified patent and that said Letters Patent is hereby corrected as shown below:

Column 11,
Lines 19, 20, 22 and 23, "The N-alpha trifluoroethyl amino acid ester compound of claim 7" should read -- The N-alpha trifluoroethyl amino acid ester compound of claim 8 --.
Line 45, "The peptide of claim 12" should read -- The peptide of claim 13 --.

Column 12,
Line 27, "The peptide of claim 17" should read -- The peptide of claim 15 --.
Line 31, "The peptide of claim 15" should read -- The peptide of claim 13 --.

Signed and Sealed this

Sixteenth Day of August, 2005

JON W. DUDAS
*Director of the United States Patent and Trademark Office*